(12) United States Patent
Lee et al.

(10) Patent No.: US 10,161,911 B2
(45) Date of Patent: Dec. 25, 2018

(54) DIAGNOSIS DEVICE FOR JOINT OF SHEET METAL AND METHOD OF DIAGNOSING DEFECT OF JOINT OF SHEET METAL USING THE SAME

(71) Applicant: KOREA INSTITUTE OF MACHINERY & MATERIALS, Daejeon Metropolitan (KR)

(72) Inventors: Jong O Lee, Gumi-Si (KR); No Hoe Ju, Changwon-Si (KR); Hyun Sup Jee, Changwon-Si (KR)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 775 days.

(21) Appl. No.: 14/268,129

(22) Filed: May 2, 2014

(65) Prior Publication Data

US 2014/0330527 A1    Nov. 6, 2014

(51) Int. Cl.
*G01N 29/11*    (2006.01)
*G01N 29/24*    (2006.01)
*G01N 29/48*    (2006.01)

(52) U.S. Cl.
CPC ......... *G01N 29/11* (2013.01); *G01N 29/2468* (2013.01); *G01N 29/48* (2013.01); *G01N 2291/0237* (2013.01); *G01N 2291/044* (2013.01)

(58) Field of Classification Search
CPC ..... G01N 29/11; G01N 29/2468; G01N 29/44
USPC .......................................................... 702/39
See application file for complete search history.

(56) References Cited

U.S. PATENT DOCUMENTS

2004/0245315 A1*  12/2004  Maev ................... G01N 29/262
                                                              228/8
2009/0151457 A1*   6/2009  Iizuka .................... G01N 29/07
                                                              73/622

FOREIGN PATENT DOCUMENTS

KR        2002843340000           3/2003

\* cited by examiner

*Primary Examiner* — Mohamed Charioui
(74) *Attorney, Agent, or Firm* — Loza & Loza, LLP; Heidi L. Eisenhut

(57) ABSTRACT

There is provided a diagnosis device of a joint of sheet metal, including: a detector that irradiates an ultrasonic wave to a diagnosis object including a first medium and a second medium having a joint, and senses a reflection signal reflected from the joint and a reflection signal reflected from the joint and thereafter, reflected toward the joint on an inner surface of the first medium; a delay material positioned between the detector and the diagnosis object to delay the reflection signal; and a diagnoser that calculates and displays a signal ratio by receiving the reflection signals sensed by the detector.

7 Claims, 10 Drawing Sheets

FIG. 9

DIAGNOSIS DEVICE FOR JOINT OF SHEET METAL AND METHOD OF DIAGNOSING DEFECT OF JOINT OF SHEET METAL USING THE SAME

CROSS-REFERENCE TO RELATED APPLICATIONS

This application claims the priority of Korean Patent Application No. 2013-49176 filed on May 2, 2013, in the Korean Intellectual Property Office, the disclosure of which is incorporated herein by reference.

BACKGROUND OF THE INVENTION

Field of the Invention

The present invention relates to a diagnosis device for a joint of sheet metal and a method of diagnosing a defect of a joint of sheet metal using the same, and more particularly, to a diagnosis device for a joint of sheet metal and a method of diagnosing a defect of a joint of sheet metal using the same that can diagnose the defect of the joint regardless of an ultrasonic wave irradiation condition by calculating and displaying amplitude ratios of reflection signals reflected from the joint at the time of irradiating an ultrasonic wave to the joint of sheet metal to be diagnosed.

Description of the Related Art

In general, as a means for securing stability of steel facilities or evaluating the quality of a product having a steel structure, inspecting whether a defect such as a crack occurs in a test member by ultrasonic detection is required.

An inspection method by the detection is generally divided into two methods, and universally, one method performs inspection while a person directly brings an ultrasonic sensor into contact with a test object and the other method is an automatic inspection method using a robot.

Meanwhile, when the ultrasonic sensor is brought into contact with the test object, an ultrasonic wave generated from an apparatus may be transferred to the inside of the test object only by closely contacting the sensor and the test object, but practically, it is substantially impossible to fully make the sensor come in close contact with the test object.

Due to such a technical problem, a detection method is used, which injects a medium made of a liquid between the sensor and the test object to transfer the ultrasonic wave generated from the sensor through the medium and in this case, the used medium may be diversified, but a so-call immersion testing method using water is in common use, which is suitable for automatic detection.

FIG. 1 which is accompanied illustrates a signal for evaluating integrity of a joint in an automatic examination method using a conventional immersion testing method and the immersion testing method measures an amplitude of a signal reflected from the joint to evaluate the integrity.

However, the immersion testing method is difficult to use when the test object cannot be dipped into water or has a complicated shape, and as a result, automatic examination is difficult.

Therefore, as illustrated in FIG. 2, Korean Utility Model Registration No. 20-0284334 discloses 'a water circulation device of a jig for ultrasonic detection' that enables detection by making water as a contact medium flow from a water tank 1 by using a pump 3 and thereafter, supplying the water onto the surface of a test object E through the bottom of a jig 2 and collect the water while maintaining airtightness.

However, the convention art has a complicated shape, and as a result, it is impossible for the conventional art to examine a test object which the ultrasonic wave is difficult to be irradiated.

Further, since contact force or a contact state of the jig 2 cannot be maintained under a predetermined condition, the sensor 5 is difficult to detect an accurate joining state of the test object E, and as a result, an ultrasonic detector 4 may inaccurately evaluate the integrity of the test object E.

SUMMARY OF THE INVENTION

The present invention has been made in an effort to provide a diagnosis device of a joint of metal sheet and a method of diagnosing a defect of a joint of metal sheet using the same that can diagnose the defect of the joint regardless of an ultrasonic wave irradiation condition by calculating and displaying amplitude ratios of reflection signals reflected from the joint at the time of irradiating an ultrasonic wave to the joint of sheet metal to be diagnosed.

Further, the present invention has been made in an effort to provide a diagnosis device of a joint of metal sheet and a method of diagnosing a defect of a joint of metal sheet using the same that enable more accurate diagnosis by definitely distinguishing reflection signals by delaying the reflection signals with a delay material.

An exemplary embodiment of the present invention provides a diagnosis device of a joint of sheet metal, including: a detector that irradiates an ultrasonic wave to a diagnosis object including a first medium and a second medium having a joint, and senses a reflection signal reflected from the joint and a reflection signal reflected from the joint and thereafter, reflected toward the joint on an inner surface of the first medium; a delay material positioned between the detector and the diagnosis object to delay the reflection signal; and a diagnoser that calculates and displays a signal ratio by receiving the reflection signals sensed by the detector.

The delay material may be configured to distinguish a reflection signal of the surface of the first medium, and a first reflection signal and a second reflection signal of the joint by delaying a time required for the ultrasonic wave irradiated from the detector to reach the diagnosis object.

The diagnoser may display a calculation value F corresponding to a ratio of the reflection signals sequentially reflected from the joint by a numerical value or a distribution.

The calculation value F may have a relationship equation of Rb (a joint reflection coefficient in which an ultrasonic wave transmits a first medium and thereafter, is reflected from the joint)×Rs (a first medium inner surface reflection coefficient in which an ultrasonic wave is reflected on an inner surface of the first medium and irradiated to the joint).

Another exemplary embodiment of the present invention provides a method of diagnosing a defect of a joint of sheet metal using a diagnosis device of a joint of sheet metal, including: a device preparation step of preparing a sheet metal joint diagnosis device including a detector that irradiates an ultrasonic wave to a diagnosis object including a first medium and a second medium having a joint, and senses a reflection signal reflected from the joint and a reflection signal reflected from the joint and thereafter, reflected toward the joint on an inner surface of the first medium, a delay material positioned between the detector and the diagnosis object to delay the reflection signal, and a diagnoser that calculates and displays a signal ratio by receiving the reflection signals sensed by the detector; an ultrasonic wave irradiating step of irradiating an ultrasonic wave to a diagnosis object; and a joint diagnosis step of displaying a calculation value F corresponding to a ratio of reflection signals sequentially reflected from a joint by a numerical value or a distribution.

In the joint diagnosis step, the calculation value F may have a relationship equation of Rb (a joint reflection coefficient in which an ultrasonic wave transmits a first medium and thereafter, is reflected from the joint)×Rs (a first medium inner surface reflection coefficient in which an ultrasonic wave is reflected on an inner surface of the first medium and irradiated to the joint).

In the joint diagnosis step, the delay material may distinguish a reflection signal of the surface of the first medium, and a first reflection signal and a second reflection signal of the joint by delaying a time required for the ultrasonic wave irradiated from the detector to reach the diagnosis object.

BRIEF DESCRIPTION OF THE DRAWINGS

The above and other aspects, features and other advantages of the present invention will be more clearly understood from the following detailed description taken in conjunction with the accompanying drawings, in which:

FIG. 9 is a table illustrating an amplitude ratio measured by using the diagnosis device of a joint of metal sheet according to the present invention with respect to the diagnosis object of FIG. 4.

DETAILED DESCRIPTION OF THE PREFERRED EMBODIMENT

Hereinafter, configuration and use examples of a diagnosis device (hereinafter, referred to as a 'diagnosis device 100' of a joint of metal sheet according to the present invention will be described with reference to FIGS. 3 and 4.

Figure 1:
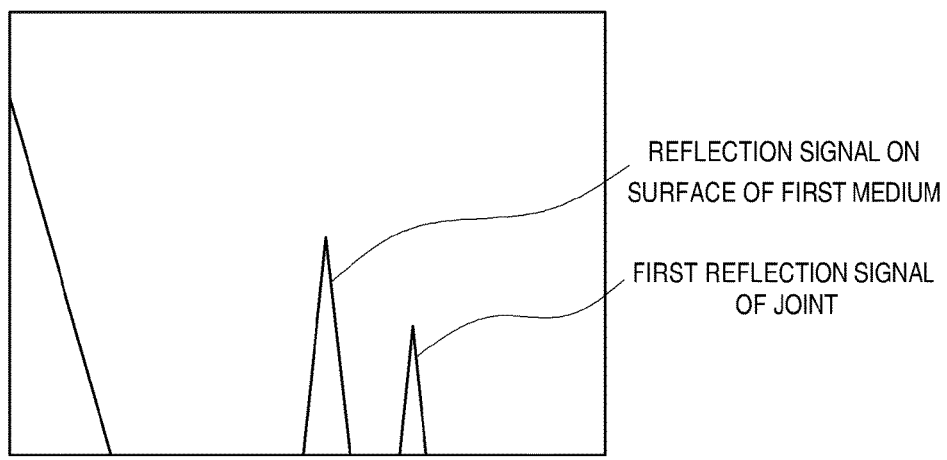
FIG. 1 is a diagram illustrating a signal for evaluating integrity of a joint of metal sheet in an automatic irradiation method using a conventional immersions testing method.
Figure 2:
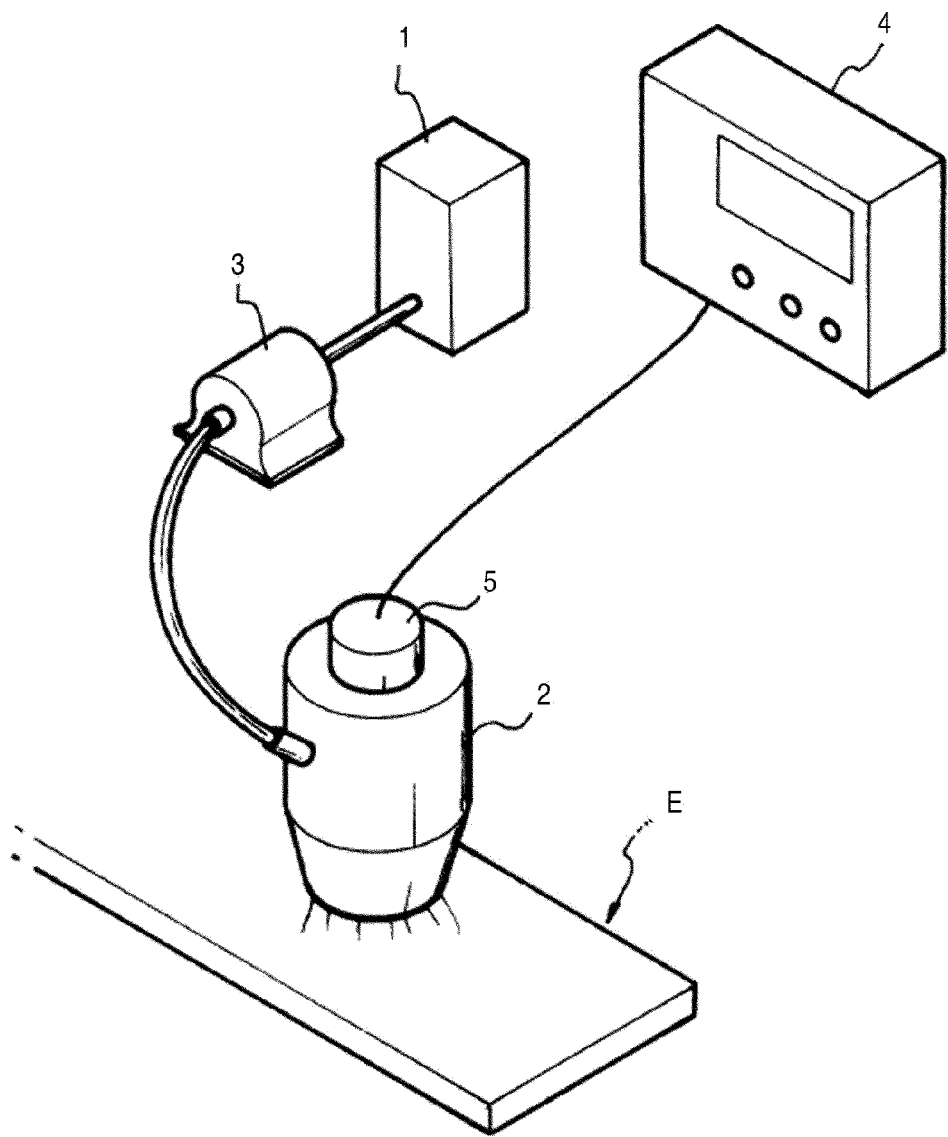
FIG. 2 is an overview diagram of a jig for ultrasonic detection disclosed in Korean Utility Model Registration No. 20-0284334.
Figure 3:
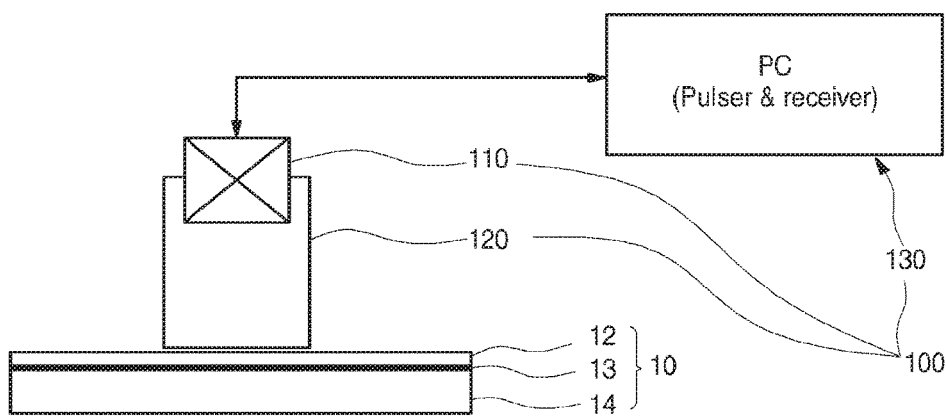
FIG. 3 is an overview diagram illustrating a configuration of a diagnosis device of a joint of sheet metal according to the present invention.

FIG. 3 is an overview diagram illustrating a configuration of a diagnosis device of a joint of sheet metal according to the present invention. FIG. 4 is a photo of an actual object illustrating a diagnosis form of the diagnosis device of a joint of sheet metal according to the present invention.

Prior to this, terms or words used in the specification and the claims should not be analyzed as a general and dictionary meaning and should be analyzed as a meaning and a concept which conform to the technical spirit of the present invention based on a principle that the inventor can appropriately define a concept of a term in order to describe his/her own invention by the most method.

Therefore, the embodiments disclosed in the specification and the configurations illustrated in the drawings are just exemplary embodiments of the present invention and do not fully represent the technical spirit. Therefore, it should be appreciated that various equivalents and modified examples capable of substituting them can be made.

As illustrated in FIG. 3, the diagnosis device 100 is positioned above a diagnosis object 10 to irradiate an ultrasonic wave.

The diagnosis object 10 adopts sheet metals of which twofolds are joined to each other in the exemplary embodiment and in more detail, is configured to include a first medium 12 positioned at an upper side, a second medium 14 positioned at a lower side, and a joint B positioned therebetween.

The diagnosis device 100 is installed above the first medium 12. The diagnosis device 100 is configured to include a detector 110 that irradiates an ultrasonic wave to the diagnosis object 10 including the first medium 12 and the second medium having the joint B, and senses a reflection signal reflected from the joint B and a reflection signal reflected from the joint B and thereafter, reflected toward the joint B on an inner surface of the first medium 12, a delay material 120 positioned between the detector 110 and the diagnosis object 10 to delay the reflection signal, and a diagnoser 130 that calculates and displays a signal ratio by receiving the reflection signals sensed by the detector 110.

The detector 110 serves to irradiate the ultrasonic wave downward and sequentially senses the reflection signals reflected from the joint B.

The delay material 120 is provided below the detector 110 to delay the reflection signals reflected from the joint B, thereby improving a sensing ability of the detector 110.

The detector 110 is electrically connected with the diagnoser 130. Therefore, the reflection signals sensed by the detector 110 are provided to the diagnoser 130 and the diagnoser 130 calculates the reflection signals according to a specific relationship equation and deduces a calculation value, and displays the deduced calculation value.

Hereinafter, detailed configurations of the detector 110 and the delay material 120 will be described with reference to FIGS. 5 and 6.

Figure 5:
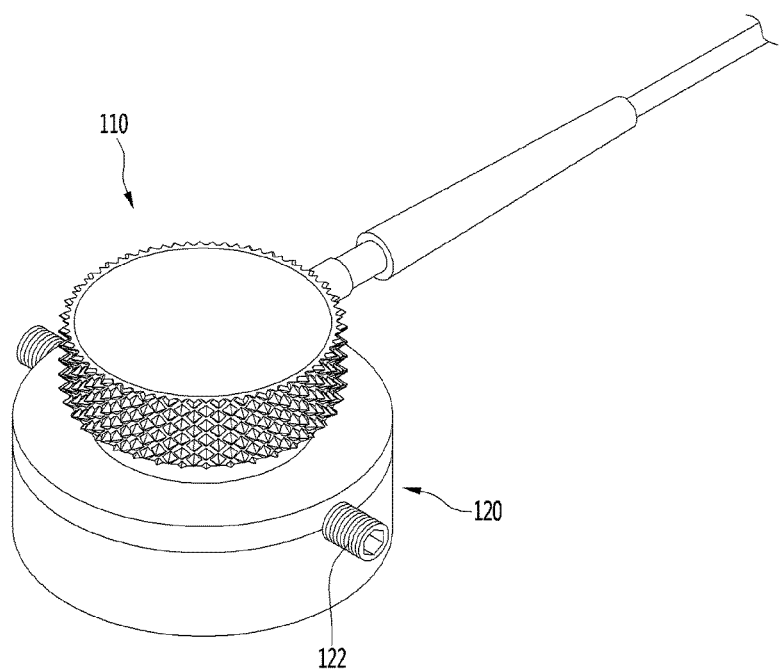
FIG. 5 is a photo of an actual object illustrating a form in which a detector and a delay material are coupled to each other as one configuration of the diagnosis device of a joint of sheet metal according to the present invention.
Figure 6:
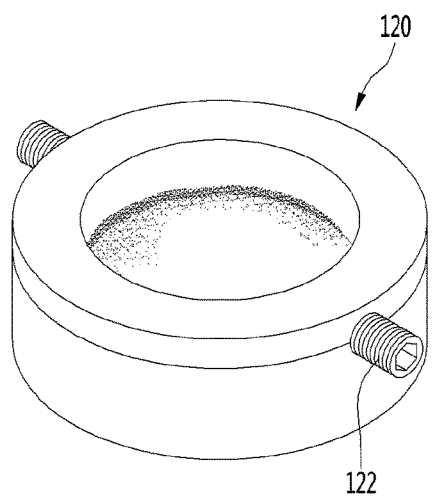
FIG. 6 is a photo of an actual object illustrating an exterior configuration of the delay material as one configuration of the diagnosis device of a joint of sheet metal according to the present invention.

FIG. 5 is a photo of an actual object illustrating a form in which a detector 110 and a delay material 120 are coupled to each other as one configuration of the diagnosis device 100 of a joint of sheet metal according to the present invention and FIG. 6 is a photo of an actual object illustrating an exterior configuration of the delay material 120 as one configuration of the diagnosis device 100 of a joint of sheet metal according to the present invention.

As illustrated in the figure, a lower part of the detector 110 is inserted into the top of the delay material 120 and the detector 110 a combination state of the detector 110 and the delay material 120 combined by a combination member 122 is maintained.

In addition, the delay material is preferably configured to be transparent so that the ultrasonic wave irradiated from the detector 110 reaches the diagnosis object 10, the delay material 120 is manufactured by an acrylic material, and the delay material 120 and the detector 110 are fixed by the combination member 122.

Further, the delay material 120 is configured to easily distinguish the reflection signal by delaying a time required for an ultrasonic wave transmission pulse irradiated from the detector 110 to reach the diagnosis object 10.

That is, the delay material 120 definitely distinguishes a surface reflection signal of a first medium 9120 by delaying a time required for the pulse irradiated from the detector 110 to reach the diagnosis object 10 to serve to accurately calculate a ratio of a first reflection signal and a second reflection signal of the joint B which are subsequent signals.

The diagnoser 130 displays a calculation value F corresponding to a ratio of reflection signals sequentially reflected from the joint B by a numerical value or a distribution, and the calculation value will be described below in detail.

Hereinafter, a method of diagnosing a defect of a joint of sheet metal using the diagnosis device 100 will be described with reference to FIG. 7.

Figure 7:
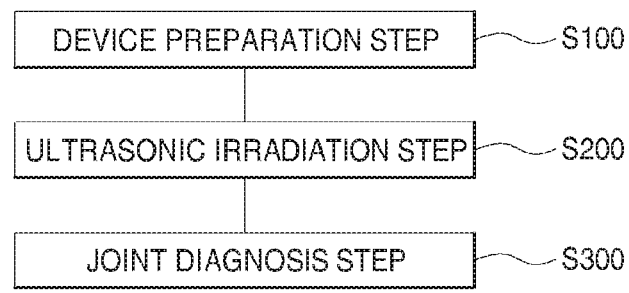
FIG. 7 is a process flowchart illustrating a method of diagnosing a defect of a joint of metal sheet using the diagnosis device of a joint of metal sheet according to the present invention.

FIG. 7 is a process flowchart illustrating a method of diagnosing a defect of a joint of metal sheet using the diagnosis device of a joint of metal sheet according to the present invention.

As illustrated in the figure, the method of diagnosing a defect of sheet metal is completed by sequentially performing a device preparation step (S100) of preparing a sheet metal joint diagnosis device 100 including a detector 110, a delay material 120, and a diagnoser 130, an ultrasonic wave irradiating step (S200) of irradiating an ultrasonic wave to a diagnosis object 10, and a joint diagnosis step (S300) of displaying a calculation value F corresponding to a ratio of reflection signals sequentially reflected from a joint B by a numerical value or a distribution.

Figure 4:
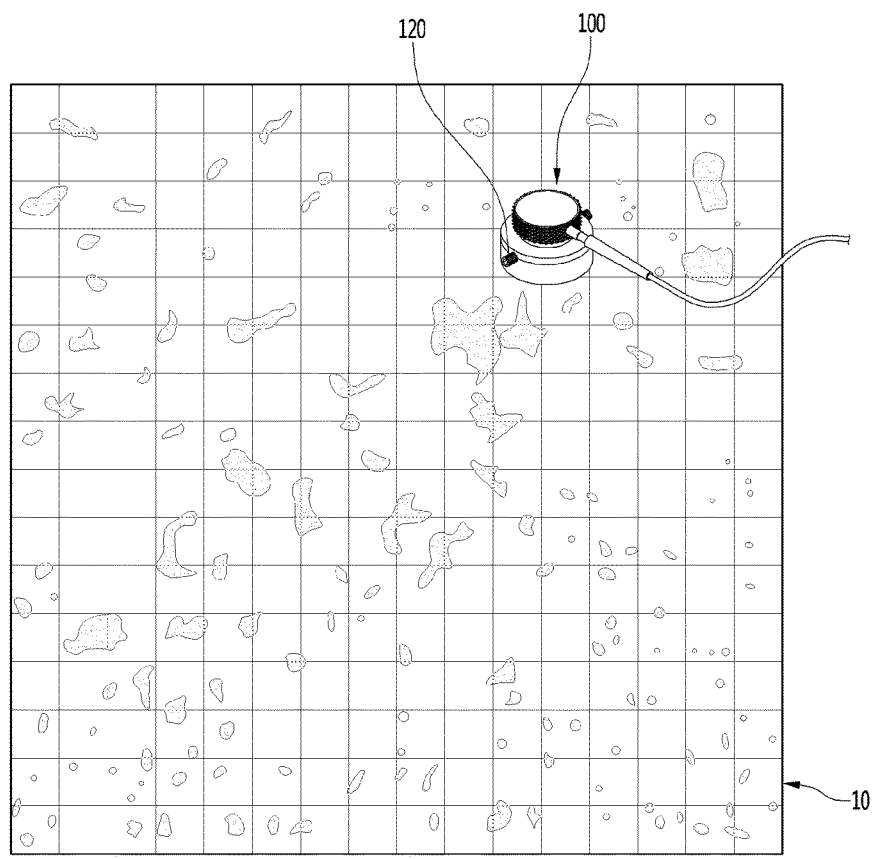
FIG. 4 is a photo of an actual object illustrating a diagnosis form of the diagnosis device of a joint of sheet metal according to the present invention.

In the device preparation step (S100), the detector 110 and the delay material 120 contact the diagnosis object 10 as illustrated in FIG. 4 in a state where the detector 110 and the delay material 120 are combined with each other as illustrated in FIG. 5.

In this case, in the diagnosis object 10 of FIG. 3, when sheet metals contact each other, centers do not contact each other and only circumferences contact each other to inspect diagnosis performance of the diagnosis device 100.

After the device preparation step (S100), the ultrasonic wave irradiation step (S200) is performed. In the ultrasonic wave scanning step (S200), the detector 110 irradiates the ultrasonic wave in a direction where the diagnosis object 10 is positioned to transmit the delay material 120.

The joint diagnosis step (S300) is performed simultaneously with the ultrasonic irradiation step (S200). In the joint diagnosis step (S300), a plurality of reflection signals is calculated in the diagnoser 130 by a relationship equation and thereafter, is displayed.

Hereinafter, a theoretical background under which the equation is deduced will be described with reference to FIG. 8.

Figure 8:
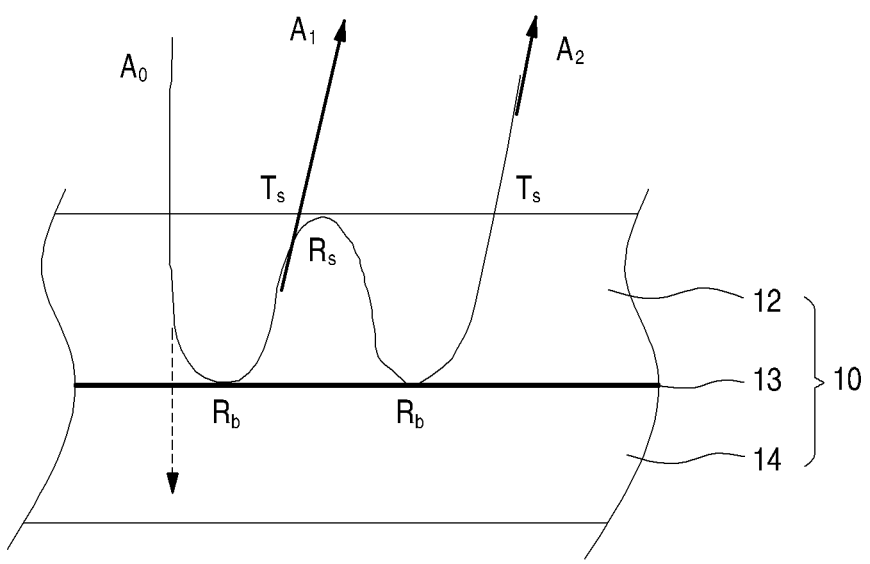
FIG. 8 is a diagram for describing a theoretical ground of a joint diagnosis step which is one step in the method of diagnosing a defect of a joint of metal sheet using the diagnosis device of a joint of metal sheet according to the present invention.

FIG. 8 is a diagram for describing a theoretical ground of a joint diagnosis step (S300) which is one step in the method of diagnosing a defect of a joint of metal sheet using the diagnosis device 100 of a joint of metal sheet according to the present invention.

First, the calculation value F has a relationship equation of Rb (a joint reflection coefficient in which an ultrasonic wave transmits a first medium 12 and thereafter, is reflected from a joint B)×Rs (a first medium inner surface reflection coefficient in which an ultrasonic wave is reflected on an inner surface of the first medium 12 and irradiated to the joint B).

In addition, symbols illustrated in FIG. 8 are as follows.

$A_0$: Amplitude of the ultrasonic wave incident in the joint B by transmitting the first medium 12 among ultrasonic waves irradiated from the detector 110
Rb: Ultrasonic wave reflection coefficient at the joint
Rs: Reflection coefficient of the inner surface of the first medium 12
$A_1$: Amplitude of a first reflection signal at the joint
$A_2$: Amplitude of a second reflection signal at the joint
Ts: Transmission coefficient of the ultrasonic wave that transmits the detector 110 from the first medium 12 through the inner surface of the first medium 12

The amplitude $A_0$ of the incident ultrasonic wave significantly varies depending on contact force or a contact state of the detector 110, the ultrasonic wave reflection coefficient Rb at the joint B varies depending on a joining state of the joint B, and Rs and Ts vary depending on a substance property of the first medium 12, but may be constants irrespective to an irradiation condition or the joining state.

In addition, in a theory of acoustics, $A_1 = A_0 Rb Ts$ and $A_2 = A_0 Rb Rs Rb Ts$ are expressed.

Therefore, a ratio of $A_1$ and $A_2$ is defined as the calculation value F and has a relationship equation as below.

$$F = A_2/A_1 = A_0 Rb^2 Rs Ts / A_0 Rb Ts = Rb Rs$$

Therefore, the calculation value F has a relationship equation of Rb (a joint reflection coefficient in which an ultrasonic wave transmits a first medium 12 and thereafter, is reflected from a joint B)×Rs (a first medium inner surface reflection coefficient in which an ultrasonic wave is reflected on an inner surface of the first medium 12 and irradiated to the joint B).

When the calculation value F is measured, the variation of Rb may be measured regardless of the ultrasonic wave irradiation condition, and Rs varies depending on the substance property of the first medium 12, but may be constants irrespective of the irradiation condition or the contact state to evaluate contact performance of the joint B.

Figure 9:
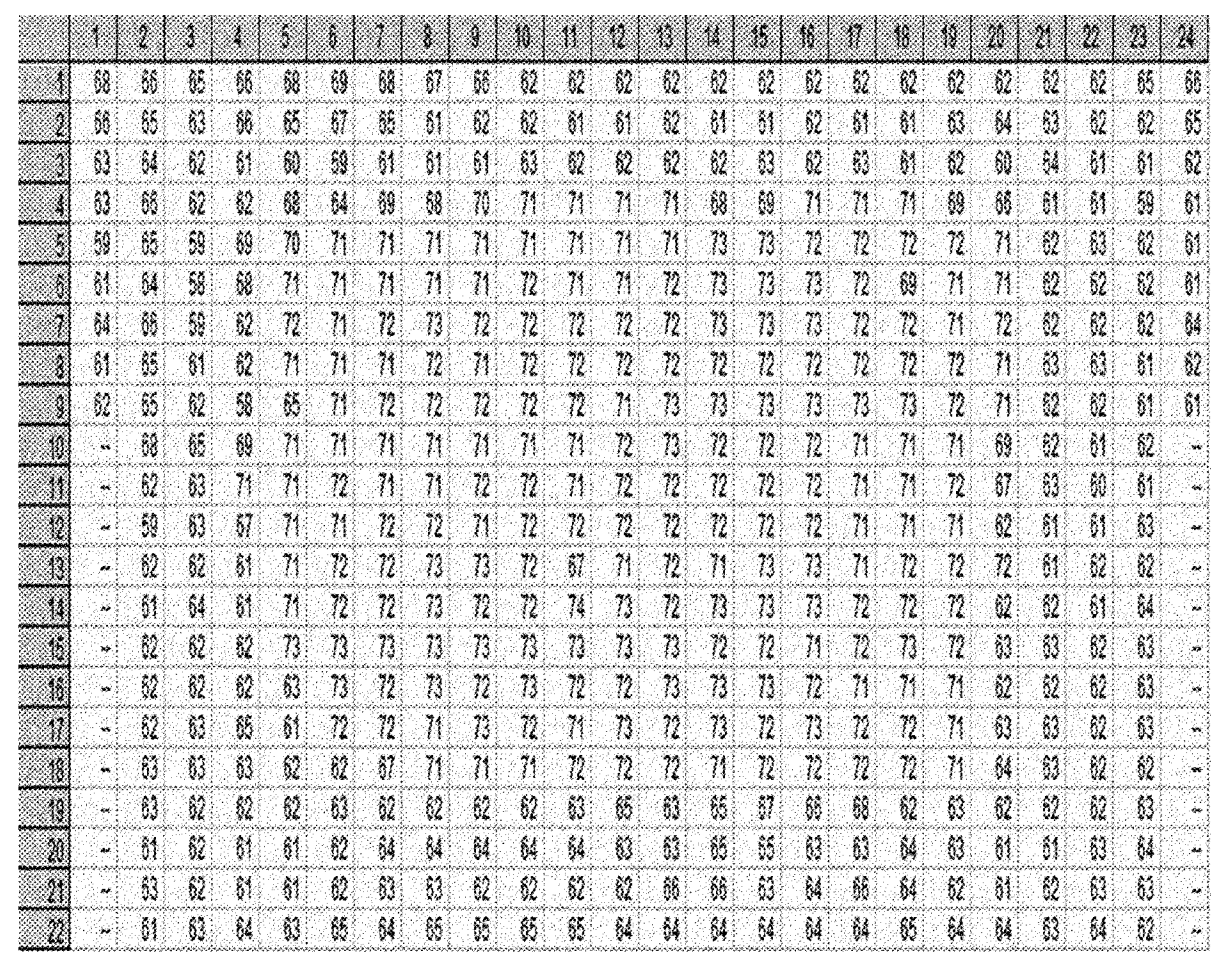

The relation equation is previously stored in the diagnoser 130, and the diagnoser 130 that sequentially receives the reflection signals sensed by the detector 110 acquires the calculation value F by making the reflection signal correspond to the reflection signal and the calculation value F for the diagnosis object 10 illustrated in FIG. 4 is illustrated in FIG. 9.

Figure 10:
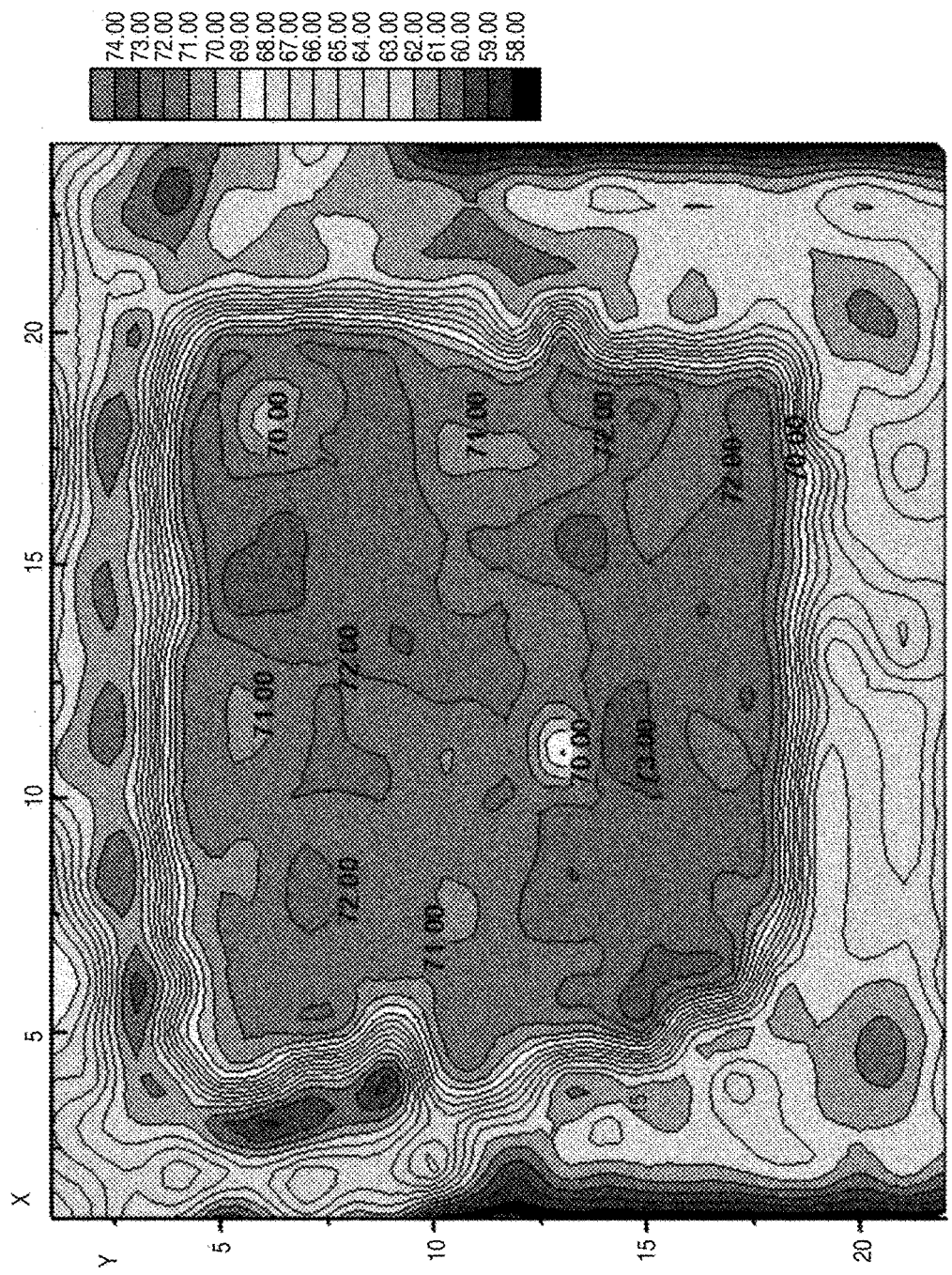
FIG. 10 is a distribution diagram visually illustrated by distinguishing data of FIG. 9 by different colors depending on a numerical value.

In addition, the data is transformable to be easily visual as illustrated in FIG. 10.

FIG. 10 is a distribution diagram visually illustrated by distinguishing data of FIG. 9 by different colors depending on a numerical value.

As illustrated in the figure, as a result of diagnosing the diagnosis object 10 in which the centers do not contact each other and only the circumferences contact each other, a contact portion and a non-contact portion show different colors to be visually verified.

The scope of the present invention is not limited to the exemplified embodiments and a lot of other transformations based on the present invention can be made by those skilled in the art within the technical scope.

For example, in the exemplary embodiment of the present invention, the diagnosis object 10 adopts a flat-panel type diagnose object to be diagnosed, but diagnosis objects 10 having various forms and exteriors can be manually diagnosed within a scope in which the delay material 120 can contact the diagnosis object 10.

As set forth above, according to exemplary embodiments of the invention, amplitude ratios of reflection signals reflected from a joint are configured to be calculated and displayed at the time of irradiating an ultrasonic wave to the joint of metal sheet which is a diagnosis object.

Therefore, since a defect of the joint can be diagnosed regardless of an ultrasonic wave irradiation condition, use convenience is improved.

Further, a diagnosis object having various exterior shapes can be diagnosed, and as a result, availability is high.

Moreover, the reflection signals are definitely distinguished by delaying the reflection signal with the delay material, and as a result, more accurate diagnosis is available.

While the present invention has been shown and described in connection with the exemplary embodiments, it will be apparent to those skilled in the art that modifications and variations can be made without departing from the spirit and scope of the invention as defined by the appended claims.

What is claimed is:

1. A diagnosis device of a joint of sheet metal, the device comprising:
    a detector that irradiates an ultrasonic wave to a diagnosis object including a first medium and a second medium having a joint, and senses a first reflection signal reflected from the joint and a second reflection signal reflected from the joint and thereafter, reflected toward the joint on an inner surface of the first medium;
    a delay material positioned between the detector and the diagnosis object to delay the first reflection signal and the second reflection signal; and
    a diagnoser that calculates and displays a signal ratio of the first reflection signal and the second reflection signal by receiving the reflection signals sensed by the detector.

2. The device of claim 1, wherein:
    the delay material is configured to distinguish an additional reflection signal of the surface of the first medium, and the first reflection signal and the second reflection signal of the joint by delaying a time required for the ultrasonic wave irradiated from the detector to reach the diagnosis object.

3. The device of claim 2, wherein:
    the diagnoser displays a calculation value F corresponding to the signal ratio of the first and second reflection signals sequentially reflected from the joint by a numerical value or as part of a distribution diagram.

4. The device of claim 3, wherein:
    the calculation value F has a relationship equation of Rb (a joint reflection coefficient in which the ultrasonic wave transmits the first medium and thereafter, is reflected from the joint)×Rs (a first medium inner surface reflection coefficient in which the ultrasonic wave is reflected on the inner surface of the first medium and irradiated to the joint).

5. A method of diagnosing a defect of a joint of sheet metal, the method comprising:
    a device preparation step of preparing a sheet metal joint diagnosis device including a detector that irradiates an ultrasonic wave to a diagnosis object including a first medium and a second medium having a joint, and senses a first reflection signal reflected from the joint and a second reflection signal reflected from the joint and thereafter, reflected toward the joint on an inner surface of the first medium, a delay material positioned between the detector and the diagnosis object to delay the first reflection signal and the second reflection signal, and a diagnoser that calculates and displays a signal ratio of the first reflection signal and the second reflection signal by receiving the first and second reflection signals sensed by the detector;
    an ultrasonic wave irradiating step of irradiating the ultrasonic wave to the diagnosis object; and
    a joint diagnosis step of displaying a calculation value F corresponding to the signal ratio of the first and second reflection signals sequentially reflected from the joint by a numerical value or as part of a distribution diagram.

6. The method of claim 5, wherein:
    in the joint diagnosis step,
    the calculation value F has a relationship equation of Rb (a joint reflection coefficient in which the ultrasonic wave transmits the first medium and thereafter, is reflected from the joint)×Rs (a first medium inner surface reflection coefficient in which the ultrasonic wave is reflected on the inner surface of the first medium and irradiated to the joint).

7. The method of claim 5, wherein:
    in the joint diagnosis step,
    the delay material distinguishes an additional reflection signal of the surface of the first medium, and the first reflection signal and the second reflection signal of the joint by delaying a time required for the ultrasonic wave irradiated from the detector to reach the diagnosis object.

* * * * *